United States Patent [19]

Pak et al.

[11] Patent Number: 4,851,221

[45] Date of Patent: Jul. 25, 1989

[54] LIQUID CALCIUM SUPPLEMENTATION FROM READILY SOLUBLE MIXTURES OF CALCIUM COMPOUND AND CITRIC ACID

[75] Inventors: Charles Y. C. Pak, Dallas; Neill B. Walsdorf, San Antonio, both of Tex.

[73] Assignees: Mission Pharmacal Company, San Antonio; Board of Regents, The University of Texas System, Austin, both of Tex.

[21] Appl. No.: 935,666

[22] Filed: Nov. 26, 1986

Related U.S. Application Data

[63] Continuation-in-part of Ser. No. 703,196, Feb. 19, 1985, abandoned, and a continuation-in-part of Ser. No. 807,530, Dec. 11, 1986, Pat. No. 4,772,467, and a continuation-in-part of Ser. No. 840,884, Mar. 18, 1986, abandoned, and a continuation-in-part of Ser. No. 896,651, Aug. 13, 1986, Pat. No. 4,814,177.

[51] Int. Cl.$^4$ .............................................. A61K 33/00
[52] U.S. Cl. ..................................... 424/693; 514/891; 424/687; 424/694
[58] Field of Search ........................ 424/127; 514/891

[56] References Cited

U.S. PATENT DOCUMENTS

| | | | |
|---|---|---|---|
| 2,953,459 | 9/1960 | Diller | 530/323 |
| 3,105,792 | 10/1963 | White | 424/44 |
| 3,653,914 | 4/1972 | Schimdt | 426/302 |
| 4,107,346 | 8/1978 | Kravitz | 426/648 |
| 4,185,093 | 1/1980 | Carnes et al. | 424/678 |
| 4,214,996 | 7/1980 | Buddemmeyer et al. | 252/1 |
| 4,289,750 | 9/1981 | Kopp et al. | 424/478 |
| 4,405,596 | 9/1983 | Helbig et al. | 424/478 |
| 4,551,342 | 11/1985 | Nuhel | 426/548 |
| 4,614,648 | 9/1986 | Bru | 424/44 |

FOREIGN PATENT DOCUMENTS

| | | |
|---|---|---|
| 0052677 | 6/1982 | European Pat. Off. . |
| 0075429 | 3/1983 | European Pat. Off. . |
| 0117653 | 9/1984 | European Pat. Off. . |
| 761525 | 12/1944 | Fed. Rep. of Germany . |
| 1915509 | 2/1971 | Fed. Rep. of Germany . |
| 3014503 | 10/1980 | Fed. Rep. of Germany . |
| 4384M | 8/1966 | France . |
| 7100516 | 6/1969 | Japan . |
| 193065 | 1/1938 | Switzerland . |
| 597936 | 2/1948 | United Kingdom . |

OTHER PUBLICATIONS

Packett, et al., (1968) *J. Animal Science* 27:1716–1721.
Pak et al. (*Res. Dir. in Comp. Path.*, pp. 215–240 (1986)).
Pak et al. (*Amer. J. Med.*, 69:19–30, (1980)).
Pak and Holt (*Metabolism*, 25:665–673 (1976)).
Rote Liste (1961), Edito Cantor (Aulendorf, Wurtt., DE) "Calceno", p. 146.
International Search Report for PCT/US 87/03066 dated 20/04/88.
WO85/05552 International Publication Dec. 19, 1985.
PCT International Search Report.
Packett et al. (date unavailable) pp. 1716–1720.
Rubin Newspaper Clipping (Austin American Stateman, 11/15/85).
Harvey et al. (J. Clin. Endocrin. Met., 61:1223 (1985)).
Nicar and Pak (J. Clin. Endocrin. Met., 61:391 (1985)).

*Primary Examiner*—John W. Rollins
*Attorney, Agent, or Firm*—Arnold, White & Durkee

[57] ABSTRACT

The present invention comprises a composition of matter consisting essentially of citric acid and one or more calcium compounds selected from the group consisting of calcium hydroxide, calcium carbonate and calcium oxide. The composition of matter is preferably a substantially dry mixture which may be used, for example, as a powder for making an "instant" beverage of potable liquid. A preferred calcium compound/citric acid molar ratio in the composition of matter of the present invention is between about 0.6 and about 1.5.

In a most preferred embodiment, the composition of matter of the present invention consists essentially of calcium hydroxide and citric acid having a calcium compound/citric acid or calcium hydroxide/citric acid molar ratio of about 1.25.

The composition of matter of the present invention has a utility demostrated by dissolution in water to form a liquid dietary calcium supplement comprising soluble calcium citrate. This composition of matter may comprise one or more of a flavorant, lubricant, sweetener or colorant usable to maintain a powdery texture or to enhance the flavor of a beverage prepared therefrom.

20 Claims, No Drawings

LIQUID CALCIUM SUPPLEMENTATION FROM READILY SOLUBLE MIXTURES OF CALCIUM COMPOUND AND CITRIC ACID

BACKGROUND OF THE INVENTION

Research leading to development of the present invention was supported in part by grants P01-AM20543 and P01-AM16061 from the National Institutes of Health, Department of Health and Human Services, United States of America.

This application is a continuation-in-part of copending applications Ser. Nos. 703,196 filed Feb. 19, 1985, abandoned; and a continuatin-in-part of 807,530 filed Dec. 11, 1986, U.S. Pat. No. 4,772,467; and a continuation-in-part of Ser. No. 840,884 filed Mar. 18, 1986, abandoned; International application number PCT/US86/00314, filed Feb. 19, 1986; and a continuation-in-part of Ser. No. 896,651 filed Aug. 13, 1986, U.S. Pat. No. 4,814,177, all incorporated by reference herein.

The mineral calcium is an important human dietary component. Calcium is required for adequate bone formation and maintenance, as well as for diverse metabolic functions. These diverse metabolic functions of calcium are incompletely understood but likely to involve, at least in part, the alteration and functional control of proteins such as enzymes.

An assurance of adequate dietary calcium intake is thus important for normal development, metabolism and maintenance. Dietary calcium intake alone however is insufficient to assure that adequate calcium levels are available for required body functions. Dietary calcium must be absorbed from the digestive tract before it may be utilized. Furthermore, the urinary excretion of absorbed calcium must be considered, particularly for individuals who may be subject to the formation of calcium-containing kidney stones.

The intestinal absorption of calcium is enhanced by vitamin D and may also be affected by the particular chemical form of ingested calcium.

Among the conditions of particular relevance to calcium dietary requirements is osteoporosis. Osteoporosis, a condition characterized by decreases in bone mass, renders bones more fragile and susceptible to fracture. The increasingly older population of this country, since osteoporosis is usually an age-related phenomenon, further accentuates the significance of this condition. Postmenopausal women are generally agreed to be most susceptible to osteoporosis. As demonstrated by Heaney et al., (J. Lab. Clin. Med. (1978) Vol. 92 No. 6 pp. 953 to 963), postmenopausal women, unless treated with estrogens, required an increased calcium intake to maintain a zero calcium balance. This increased required intake was ascribed as due to a decrease in the production of an active vitamin D compound and calcium absorption, both perhaps related to the absence of estrogens. Recker et al., (Annals Int. Med. (1977) Vol. 87 No. 6 pp. 649 to 655) demonstrated that further bone losses in osteoporosis prone postmenopausal women may be prevented by estrogen treatment or, to a lesser extent, by dietary calcium carbonate supplementation.

In an additional study concerning osteoporosis of postmenopausal women, Nordin et al., (Brit. Med. J. (1980) Vol. 280 pp. 451 to 454) found three treatments that succeeded in lessening or abolishing further bone deterioration. These three treatments were: dietary calcium supplementation; estrogenic hormone treatment; and, treatment with estrogenic hormone plus 1 alpha hydroxy vitamin $D_3$.

Treatment of individuals with estrogenic hormones may have adverse effects, such as the stimulation of estrogen-dependent tumors. Treatment of individuals with vitamin D derivatives may be inadvisable because of potentially toxic effects when excess vitamin D is administered. An effective dietary calcium supplementation appears to be an advisable treatment for osteoporosis.

In certain individuals however, dietary calcium supplementation may increase urinary calcium and lead to formation of calcium-containing kidney stones (nephrolithiasis).

Kidney stone formation may result from a number of conditions, one of which is the presence of undue amounts of calcium in urine. Pak et al., (N. Eng. J. Med. (1974) Vol. 290 pp. 175 to 180) have shown that urinary calcium levels and renal calcium stone formation are decreased when patients with a history of recurrent calcium nephrolithiasis are fed low calcium diets and treated orally with cellulose phosphate. Pak (Urolithiasis Research (1976) ed. by H. Fleisch et al., Plenum Pub. Co., N.Y., N.Y. pp. 213 to 224) demonstrated that when patients with absorptive hypercalciuria are fed calcium gluconate, they exhibited increased urinary calcium, leading to an increased activity product ratio, a measure of the degree of urinary calcium oxalate saturation. Thus, calcium supplementation made them more prone to form kidney stones, since their urine became more supersaturated with respect to a common stone salt (calcium oxalate).

Belizan et al., (J. Am. Med. Ass'n. (1983) Vol. 249 No. 9 pp. 1161 to 1165) indicated that young adults showed reduction in blood pressure when their diets were supplemented with 1 gm/day elemental calcium (calcium carbonate and calcium lactate-gluconate). A similar observation was made with pregnant women (Belizan et al., Am. J. Obstet. Gynecol (1983) Vol. 146 No. 2 pp. 175 to 180). Currently, a possibility exists that adequate calcium intake may be an important factor in control of blood pressure. Additionally, it has been proposed that the incidence of colon cancer may be lessened by increases in dietary calcium intake.

Chronic diarrheal syndrome, where bone loss may occur, also sometimes involves calcium nephrolithiasis. This syndrome may result from surgical resection or inflammation of the digestive tract. Bone disease may occur because patients with this condition absorb calcium poorly from intestines. Kidney stones may develop from different causes including concentrated urine, undue acidity of urine and low urinary citrate. While these patients require calcium supplements for prevention of bone loss, they face the danger of forming more kidney stones when they take more calcium.

Supplementation of the diet with calcium appears to be an important step for control of adverse conditions including osteoporosis, bone loss in chronic diarrheal syndrome and possibly at least certain types of hypertension and colon cancer. Such calcium supplementation however, may cause undesirable effects, particularly nephrolithiasis.

Dietary calcium supplementation is generally agreed as most effective when the calcium is efficiently absorbed from the digestive tract. Thus a method of providing efficiently absorbed calcium while inhibiting calcium nephrolithiasis is needed.

The following is a more detailed clinical description of some of above conditions, as well as a description for additional conditions, in which calcium citrate (especially in the special liquid form as embodied in this invention) may be useful.

Hypoparathyroidism. Hypoparathyroidism (either parathyroid hormone-deficient or resistant) is characterized clinically by hypocalcemia (low blood calcium from impaired skeletal mobilization and intestinal absorption of calcium) and hyperphosphatemia (high blood phosphate from defective renal phosphate clearance) (Breslau and Pak, Metabolism, Vol. 28, pp 1261–1276, 1979). It has been customary to provide calcium supplementation and exogenous vitamin D substances to correct these disturbances.

While there has been considerable progress in the therapeutic management with the introduction of active vitamin D metabolite (1,25-(OH)$_2$vitamin D) in the marketplace, three areas continue to be of some concern. First, some patients may show variable response to 1,25-(OH)$_2$vitamin D and may sometimes develop hypercalcemia/hypocalcemia. Second, substantial hypercalciuria (high urinary calcium) may ensue when normal serum calcium concentration is restored by treatment. Some patients may develop kidney stones. Third, serum phosphorus may remain high, especially when vitamin D substances are given. The need for a calcium supplement, which provides available calcium as well as bind phosphate, would seem to be clear.

Postmenopausal Osteoporosis. Considerable interest has been generated recently concerning potential therapeutic role of calcium supplements in the prevention of postmenopausal osteoporosis. The rationale for the use of calcium supplements in postmenopausal osteoporosis is the finding that calcium absorption is often depressed, presumably because of the defective renal synthesis of 1,25-(OH)$_2$ vitamin D. Thus, a higher calcium intake is needed by postmenopausal women to prevent negative calcium balance. Heaney et al., (J. Lab. Clin. Med., Vol. 92, p 953, 1978), showed that the amount of calcium intake required to achieve zero calcium balance increased by approximately 500 mg/day to nearly 1500 mg/day with the onset of menopause. Their study provided experimental basis for the recommendation by the recent Consensus Development Conference on Osteoporosis that calcium intake of 1000–1500 mg/day be provided in order to "reduce the incidence of osteoporosis in postmenopausal women." Since the average dietary calcium intake of postmenopausal American women is only about 500 mg/day, the need for calcium supplementation would seem to be clear.

End-stage Renal Disease. The pathogenetic mechanisms responsible for the development of renal osteodystrophy are multifactorial. They include renal phosphate retention, intestinal malabsorption of calcium, renal aluminum retention and acidosis. There is some evidence that these disturbances could be ameliorated by calcium citrate therapy.

Considerable evidence supports the view that phosphate retention plays a major role in the development of secondary hyperparathyroidism in renal failure. Phosphate retention, resulting from a reduction in glomerular filtration rate, may cause a transient decline in serum calcium concentration in mild-moderate renal disease. In an attempt to normalize serum calcium and phosphorus levels, parathyroid hormone secretion is increased, leading to secondary hyperparathyroidism. When the glomerular filtration rate declines to less than 25% of normal, significant hyperphosphatemia may supervene because of inadequate compensation by parathyroid stimulation. Secondary hyperparathyroidism accounts for the development of osteitis fibrosa (bone destruction), whereas hyperphosphatemia contributes to soft tissue calcification.

The intestinal calcium absorption is typically reduced in end stage renal disease, largely due to the defective renal synthesis of 1,25-(OH)$_2$vitamin D. The reduced intestinal calcium absorption contributes to the development of secondary hyperparathyroidism. Exogenous 1,25-(OH)$_2$vitamin D may restore normal intestinal calcium absorption, but may be complicated by frequent development of hypercalcemia (high blood calcium).

Although aluminum metabolism in normal persons is poorly understood, previous studies have demonstrated that intestinal absorption and renal excretion normally play a key role in aluminum metabolism. Aluminum toxicity is rare in persons with normal renal function because of efficient renal elimination. With the loss of renal function, however, aluminum accumulates in the body, especially in bone. Bone biopsy specimens from dialysis patients demonstrated a strong correlation between the presence of osteomalacia (impaired mineralization of bone) and elevated levels of aluminum in bone (Hodsman et al., Ann. Int. Med., Vol. 94, pp. 629–637, 1981). There is substantial experimental evidence supporting the view that aluminum accumulation in bone causes osteomalacia.

Initial reports of aluminum intoxication resulting in osteomalacia were in patients undergoing dialysis with dialysate prepared from tap water containing high levels of aluminum. The establishment of standards for permissible levels of aluminum in dialysate (less than 10 ug per liter) resulted in a decrease in these diseases from previously epidemic proportions and it was believed that aluminum toxicity would no longer afflict patients on chronic hemodialysis. Unfortunately, this has not been the case. Phosphate binding gels, principally aluminum hydroxide, have been used to prevent the hyperphosphatemia in chronic renal failure and thus preventing the secondary hyperparathyroidism. Unfortunately, evidence now suggests that the aluminum load delivered to chronic renal failure patients from aluminum-containing phosphate binders results in aluminum accumulation in the body causing a vitamin D resistant osteomalacia.

Metabolic acidosis frequently complicates the course of chronic renal disease because of defective renal elimination of acid. Loss of bone mass may ensue, possibly because of the need to buffer the acid load by bone mineral. It has been customary to provide soluble alkali to correct the acidosis. However, the typical alkali used, citrate or bicarbonate salts of sodium and potassium, impose a load of these cations which may not be advantageous or safe in patients with end stage renal disease.

Essential Hypertension. There is some evidence that dietary calcium suplements may be beneficial in essential hypertension. Diet histories have disclosed a lower calcium intake among patients with essential hypertension. Serum ionized calcium has been reported to be low in the low renin subtype. Calcium supplements have been reported to reduce blood pressure in preliminary trials in control subjects, pregnant women, and patients with essential hypertension.

There is some evidence for the varying vasopressor effects of the different types of monovalent cation and anions. The association of dietary sodium and hypertension is long recognized. On the other hand, potassium may have a protective role on blood pressure (Iimura et al., Clin. Sci., Vol. 61, pp 77–80, 1981). Recently, a hypertensive role of chloride ion has been implicated. In contrast, bicarbonate ion even when given as the sodium salt has been shown to be protective against the development of hypertension. The varying effect of anions may be explained by the retardation of calcium influx by alkali.

SUMMARY OF THE INVENTION

The present invention comprises a composition of matter consisting essentially of citric acid and one or more calcium compounds selected from the group consisting of calcium hydroxide, calcium carbonate and calcium oxide. This composition of matter preferably comprises citric acid and one or more calcium compounds selected from the group consisting of calcium hydroxide, calcium carbonate and calcium oxide. The composition of matter is preferably a substantially dry mixture which may be used, for example, as a powder for making an "instant" beverage of potable liquid. A preferred calcium compound/citric acid molar ratio in the composition of matter of the present invention is between about 0.6 and about 3.0. In a more preferred embodiment, the composition of matter of the present invention consists essentially of a mixture of calcium hydroxide and citric acid having a calcium compound/citric acid ratio of about 1.25, most preferably, a mixture of calcium hydroxide and citric acid having a calcium hydroxide/citric acid molar ratio of about 1.25.

The composition of matter of the present invention has a utility demonstrated by dissolution in water to form a liquid dietary calcium supplement comprising soluble calcium citrate preferably enriched with citric acid. This composition of matter may comprise one or more of a flavorant, lubricant, sweetener or colorant usable to maintain a powdery texture or to enhance the flavor and appearance of a beverage prepared therefrom.

The present invention also involves a method for preparing a mixture soluble in an aqueous solvent to form a potable liquid consisting essentially of calcium citrate and citric acid. This method comprises the steps of: mixing a calcium compound (preferably calcium hydroxide) and citric acid in a calcium compound/citric acid molar ratio of between about 0.6 and about 3.0, preferably between about 0.6 and about 1.5 and most preferably about 1.25.

This potable liquid consisting essentially of calcium citrate and citric acid may be prepared by dissolving a quantity of said above-described mixture in an amount of aqueous solvent such as tap water. Such a potable liquid is suitable for the dietary supplementation of calcium without substantial risk of calcium renal stone facilitation or enhancement. The potable liquid consists essentially of: citric acid; water; and a calcium compound selected from the group consisting of calcium hydroxide, calcium oxide and calcium carbonate. The potable liquid preferably has a pH between about 2 and about 7, more preferably between about 3 and about 5. The potable liquid preferably comprises calcium compound and citric acid are in a calcium compound/citric acid molar ratio between about 0.6 and about 1.5. This potable liquid preferably compries calcium in an concentration between about 500 mg/L and about 2000 mg/L and contains calcium hydroxide as the calcium compound.

DESCRIPTION OF THE PREFERRED EMBODIMENT

The present invention presents evidence that mixtures of citric acid and a calcium compound such as calcium hydroxide as a form of liquid calcium supplementation is more optimal than tricalcium dicitrate provided in a tablet form. Although calcium hydroxide is a preferred calcium compound, it is understood that calcium oxide and calcium carbonate may be equally useful in the practice of the present invention.

In the original patent application No. 703,196 filed Feb. 15, 1985 it was shown that calcium citrate (tricalcium dicitrate) given orally in a solid form provides a greater calcium bioavailability (absorbability) and citraturic response (rise in urinary citrate) than calcium carbonate. Thus, more calcium was absorbable from calcium citrate than from a comparable amount of calcium carbonate (Nicar and Pak, J. Clin. Endo. Metab. Vol. 61, pp 391–393, 1985). Urinary citrate rose significantly during calcium citrate treatment, but not during calcium carbonate therapy (Harvey, Zobitz and Pak, J. Clin. Endo, Metab. Vol. 61, pp 1223–1225, 1985). Since citrate is an inhibitor of calcium (kidney) stone formation, results suggested tat calcium citrate treatment would be less likely than calcium carbonate to cause such stones.

Subsequent related patent application Nos. (807,530; 840,884 and 896,651), involved improved formulations of calcium citrate which possessed even greater bioavailability and citraturic effect than the original product (a solid preparation of tricalcium dicitrate). Since the solid form of calcium citrate must be dissolved in the intestinal tract before it is absorbed or raises urinary citrate, means to increase the solubility of tricalcium dicitrate were sought. Two successful approaches were discussed in these prior patent applications.

First, it was found that solid preparations of calcium citrate made with an excess of citrate (calcium/citrate molar ratio of less than 1.5 where a value of 1.5 represents the ratio for tricalcium dicitrate) had greater aqueous solubility. Thus, in a synthetic solution which mimicked gastric juice (pH 3, 37° C.), citrate-enriched calcium citrate (with calcium/citrate molar ratio of 0.67) in a solid form was 8.85 times more soluble than tricalcium dicitrate. This calcium-enriched calcium citrate was also found to be more absorbable from the intestinal tract. In three normal subjects, the rise in urinary calcium after taking this modified solid form of calcium citrate was 24% greater than following ingestion of an equivalent amount of tricalcium dicitrate.

Second, a more soluble form of calcium citrate could be prepared by pre-mixing fixed amounts of calcium hydroxide and citric acid sufficient to achieve a desired molar ratio of calcium and citrate. When added to water, the mixture readily dissolved, yielding soluble calcium and citrate without elaboration of carbon dioxide. This "pre-mix" of calcium hydroxide and citric acid was much more suitable in preparing liquid calcium preparations, than pre-formed citrate-enriched calcium citrate which took longer to dissolve.

In this continuation-in-part, additional data supporting utility of a pre-mix of calcium compound and citric acid in preparing a liquid preparation of calcium are presented. A readily soluble, powdered preparation of citric acid and a calcium compound such as calcium hydroxide, containing a desired amount of calcium, may be dissolved in an aqueous solvent such as water, fruit juice or soft drink prior to ingestion. Different mixtures with varying relative amounts of calcium compound and citric acid were tested in order to determine which demonstrated optimum solubility, calcium bioavailability and citraturic action. Such a preparation should be particularly useful in the correction of hypocalcemia in patients with hypoparathyroidism, in the prevention of bone loss in postmenopausal women, in the control of phosphate retention in patients with end-stage renal failure and in the treatment of essential hypertension.

Liquid dietary calcium supplementation, useful in the prevention or treatment of hypoparathyroidism, postmenopausal osteoporosis, phosphate retention of chronic renal failure and essential hypertension, is accomplished by a readily soluble pre-mix of citric acid and a calcium compound, preferably calcium hydroxide.

From the aforementioned actions of liquid calcium supplementation from readily solubilized premixes of calcium compound and citric acid, it should be apparent that these readily soluble mixtures should be more effective than tricalcium dicitrate (solid), or certainly calcium carbonate, in the management of various clinical disorders described earlier herein.

Calcium carbonate is the most widely used calcium supplement. There is theoretical basis for the assertion that calcium citrate may be more optimal for the treatment of hypoparathyroidism. First, calcium is more absorbable from calcium citrate than from calcium carbonate. While calcium carbonate generally requires adequate gastric acid secretion for dissolution and absorption, the absorption of calcium citrate is less dependent on acid secretion especially in its modified (readily soluble pre-mix) form. The difference in calcium absorbability between the two salts may be more marked in hypoparathyroidism, because gastric acid secretion may be impaired owing to hypocalcemia. The improved calcium bioavailability of calcium citrate may reduce the requirement for vitamin D substances.

Second, calcium citrate therapy should augment citrate excretion, especially when given in the citrate-rich form. There should be a reduced propensity for the crystallization of stone-forming calcium salts in urine due to the inhibitor activity of citrate. This action should help reduce the risk for stone formation which may sometimes complicate this condition.

Third, calcium citrate is capable of binding dietary phosphate in the intestinal lumen. This binding capacity should be greater for mixtures of calcium hydroxide and citric acid than by calcium carbonate or solid tricalcium dicitrate because of the greater or more rapid solubility of pre-mixes and availability of calcium. Thus, there should be a better control of hyperphosphatemia.

In recent reports, calcium carbonate has been shown to be ineffective in preventing vertebral bone loss in postmenopausal women (Christiansen et al., J. Bone Min. Res. 166A, 1986). Prior studies of the present inventors indicated that tricalcium dicitrate may be potentially more effective than calcium carbonate in preventing bone loss. Our prior patent application (Ser. No. 807,530) presented preliminary data showing that calcium citrate may avert further bone loss. This conclusion was derived from findings that calcium citrate (a) provides a modest but definite alkali load which may exert a protective effect against bone loss, (b) confers greater calcium bioavailability, and (c) may be associated with a reduced risk for the crystallization of stone-forming calcium salts because of citraturic response. Liquid calcium supplementation in the form of mixtures of calcium hydroxide and citric acid should be more effective than tricalcium dicitrate because of its greater solubility, bioavailability, provision of alkali load and citraturic action.

There is a sound theoretical basis for the assertion that tricalcium dicitrate therapy should ameliorate complications of chronic renal failure.

First, calcium citrate should prevent phosphate retention by binding phosphate in the intestinal tract. High doses of another calcium salt (calcium carbonate, 3–20 g calcium/day) has been shown to prevent the absorption of ingested phosphate (Clarkson et al., Clin. Sci., Sol. 30, pp 524–438, 1966). Calcium citrate may be more effective than calcium carbonate in binding phosphate in the intestinal tract and in averting phosphate retention. Before calcium can bind phosphate in the gut, calcium must be dissociated from its associated anion. Calcium citrate has a greater aqueous solubility than calcium carbonate. This fact partly accounts for the higher calcium absorbability (bioavailability) from calcium citrate. Thus, more free calcium should be available from calcium citrate than from calcium carbonate to complex phosphate in the gut. This conclusion is supported by the study of McDonald et al., (Clin. Sci., Vo. 26, pp 27–39, 1964), who found that a "modest" dose of calcium citrate (2 g calcium/day) was effective in restoring normal serum phosphate concentration in patients with renal failure. Our own preliminary data has shown that a satisfactory control of hyperphosphatemia could be achieved in the majority of patients with tricalcium dicitrate at a dose of 1.5–2.75 g calcium/day. Moreover, serum aluminum concentration declined from 127 ng/ml (before treatment) to 79 ng/ml after 8 weeks of treatment ($p < 0.05$).

Second, calcium citrate supplementation may provide sufficient calcium for absorption to avert malabsorption of calcium in patients with end stage renal disease. Calcium citrate may be more effective in this regard than calcium carbonate, the most widely-used calcium salt. Third, calcium citrate supplementation might obviate the need for the use of aluminum-containing antacids to bind phosphate, thus reducing aluminum load. The decline in serum aluminum concentration was previously enumerated. Finally, calcium citrate may ameliorate metabolic acidosis since it provides an alkali load.

The above expectations for tricalcium dicitrate should be even more applicable for the liquid calcium supplementation with mixtures of calcium hydroxide and citric acid. Because of its rapid solubility, such pre-mixes should be more effective in binding phosphate and controlling hyperphosphatemia. They should be more effective in averting secondary hyperparathyroidism because of its greater calcium absorption. There should be a better control of metabolic acidosis since higher alkali load (citrate) would be delivered.

The present invention derives in part from observations concerning the effects of calcium carbonate, tricalcium dicitrate (solid) and placebo in essential hypertension. Neither calcium carbonate nor tricalcium dicitrate (800 mg calcium/day) was effective in lowering blood pressure. It is expected that liquid calcium supplementation in the form of mixtures of calcium hydroxide and citric acid should show hypotensive action, because of its greater calcium absorbability and alkali load.

Following is a summary of studies done with pre-mixes of calcium hydroxide and citic acid, showing superior solubility and absorbability.

Several mixtures of calcium compound and citric acid were tested. Their calcium/citrate molar ratio ranged from 1.5 to 0.67. Solubility (defined as the amount of total calcium remaining in solution) was tested for these mixtures containing 500 mg calcium in 300 ml of water. The solubility was dependent on pH, time of incubation and the calcium/citrate molar ratio. All mixtures readily dissolved in water. All mixtures dissolved rapidly and remained in solution for at least 1 hour at a wide pH range (2–7). With a longer duration of incubation as well as at higher pHs, calcium precipitation occurred (as calcium citrate), leaving less calcium in solution. After 24 hours of incubation the final solubility approximated that found when corresponding solid form of calcium citrate and citric acid were used to formulate the same calcium/citrate compositions. The period required for the precipitation of calcium citrate after initial dissolution was more prolonged for citrate-rich mixtures with lower calcium/citrate ratios. The final solubility was higher for mixtures with lower calcium/citrate ratios.

The absorption of calcium from the intestinal tract, tested in normal subjects, was greater from liquid calcium formulations prepared from mixtures of calcium compound and citric acid than from a solid preparation of preformed tricalcium dicitrate. The absorption of calcium from the mixture with a calcium/citrate molar ratio of 1.5 was 27–63% greater than that from the preformed solid preparation with same molar ratio (tricalcium dicitrate). The highest bioavailability among various preparations tested was obtained with the pre-mix of calcium compound and citric acid with a calcium/citrate molar ratio of 1.25.

Ingestion of dissolved mixtures of calcium hydroxide and citric acid, especially those containing an excess of citric acid, caused a more prominent rise in urinary citrate (inhibitor of stone formation), than ingestion of a comparable amount (in terms of calcium content) of solid tricalcium dicitrate.

Thus, mixtures of citric acid and a calcium compound such as calcium hydroxide represented effective means of providing liquid calcium supplementation. They could be dissolved rapidly in an aqueous liquid or a soft drink before ingestion. The pre-mix preparation with a calcium/citrate molar ratio of 1.25 was particularly suitable because of desired citrate content (60 meq/day assuming calcium intake of 1 g/day), adequate solubility and optimum calcium bioavailability. Other mixtures with different molar ratios may be useful under special circumstances. Owing to these properties, liquid calcium supplementation provided by mixtures of a calcium compound such as calcium hydroxide and citric acid may be more useful than tablet preparations of tricalcium dicitrate for raising serum calcium concentration in hypoparathyroidism, preventing bone loss in early postmenopausal women, controlling hyperphosphatemia in renal osteodystrophy and in lowering blood pressure in calcium-sensitive essential hypertension. Moreover, it is expected that such liquid calcium supplementation would be associated with a further reduction in the risk for stone formation, due to a more prominent citraturic action.

The present invention relates to presented evidence that mixtures of citric acid and a calcium compound such as calcium hydroxide as a form of liquid calcium supplementation are more optimal than tricalcium dicitrate provided, for example, in a tablet form. Although calcium hydroxide is a preferred calcium compound, it is understood that calcium oxide and calcium carbonate may be equally useful in the practice of the present invention. A more detailed description follows.

First, mixtures of calcium hydroxide and citric acid were found to be much more rapidly soluble than tricalcium dicitrate. Solubility was determined for 500 mg calcium (representing a typical prescribed dose) in 300 ml of water (representing gastric juice volume after ingestion of water with calcium supplement) at pH 2–7. The mixtures of calcium hydroxide and citric acid, ranging in calcium/citrate molar ratio of 0.67 to 1.5, rapidly and completely dissolved in water at all pHs. Subsequently, calcium citrate precipitated out of solution. The time required for initiation of precipitation depends on the citrate content and on pH. Thus, the precipitation took place within one hour of dissolution in the case of the mixture with a calcium/citrate molar ratio of 1.5 (representing the molar ratio for tricalcium dicitrate). However, for the citrate-enriched mixture with a calcium/citrate molar ratio of 0.67, more than 2 hours were required to initiate calcium citrate precipitation. Moreover, for all mixtures, precipitation occurred at high pHs but not at low pHs. The total amount of calcium citrate precipitation was greatest for the mixture with highest calcium/citrate ratio (1.5), and smallest for the citrate-enriched mixture with calcium/citrate molar ratio of 0.67. When the precipitation was complete, the solubility of calcium citrate approximated that of the corresponding preformed calcium citrate (with same calcium/citrate ratio).

In contrast, the preformed solid preparation of tricalcium dicitrate underwent only gradual dissolution, expecially at higher pHs. The preformed solid preparations of calcium citrate with an excess of citrate (to yield calcium/citrate molar ratio of less than 1.5) had enhanced solubility. However, for these preformed solid preparations, the rate of dissolution was too slow to be useful in making liquid calcium supplements.

The final solubility of calcium citrate was the same for the precipitated material as was for the preformed compound. However, mixtures of calcium hydroxide and citric acid initially dissolved rapidly and gradually allowed precipitation of calcium citrate. In contrast, preformed solid preparations of calcium citrate gradually dissolved, yielding soluble calcium and citrate. Thus, the pre-mixes of calcium hydroxide and citric acid served as convenient means of rapidly providing calcium (and citrate) in a liquid form. By adding an excess of citric acid, the precipitation of calcium citrate could be delayed, and the preparation could be kept in a soluble form longer.

Second, calcium bioavailability (absorbability from intestines upon oral ingestion) was greater from liquid formulations prepared from mixtures of calcium hydroxide and citric acid than from solid tricalcium dicitrate. Ten normal subjects underwent indirect measures of intestinal calcium absorption four times, after receiving orally 500 mg calcium as tricalcium dicitrate (solid form), and as pre-mixes of calcium hydroxide and citric acid with molar calcium/citrate ratios of 1.5, 1.25 and 0.67 (in liquid form). The pre-mixes yielded greater absorbability of calcium than tricalcium dicitrate. The increment in urinary calcium during the second two hours after taking liquid calcium supplements was 18-74% greater than that following ingestion of solid tricalcium dicitrate, with the highest value obtained for the pre-mix with calcium/citrate molar ratio of 1.25. The calcium absorption was also measured more directly from the recovery of radiocalcium after taking labeled calcium preparations in 6 normal subjects. The intestinal calcium absorption was greater from liquid preparations made from mixtures of calcium hydroxide and citric acid than from the solid preparation of trialcium dicitrate, with the highest value being obtained for the pre-mix with a calcium/citrate molar ratio of 1.25 (70% higher).

Third, the liquid calcium supplementation in the form of pre-mixes of calcium hydroxide and citric acid should be more efficient than as a solid or tablet preparation (tricalcium dicitrate) in binding phosphate in the intestinal tract. The binding of phospate in the diet more readily occurs with calcium in a soluble state rather than in a solid or precipitated form. As previously described, calcium and citrate may be kept in a soluble form metastably beyond the theoretical and actual final solubility by using readily soluble mixtures of calcium citrate and citric acid.

Fourth, liquid calcium supplementation in the form of mixtures of calcium hydroxide and citric acid should provide a greater alkali load and citraturic response than the solid preparation of tricalcium dicitrate. Since these mixtures yield greater amounts of citrate in a soluble form, more citrate should be absorbed to provide an alkali load and to raise urinary citrate. Thus, urinary citrate rose from 107 mg/4 hours without calcium supplementation, to 137 mg/4 hours following ingestion of 500 mg calcium as pre-mix of calcium hydroxide and citric acid with a calcium/citrate molar ratio of 1.25, and to 174 mg/4 hours after taking the pre-mix with calcium/citrate molar ratio of 1.5. The citraturic response should reduce the risk for the crystallization of stone-forming calcium salts (Harvey, Zobitz and Pak, J. Clin. Endo. Metab. Vol. 62, pp 1223-1225, 1985), albeit it may not totally eliminate the risk in some instances. The alkali load provided may also be beneficial for bone. In 16 women with nephrolithiasis (due to causes other than absorptive hypercalciuria) studied, alkali load with potassium citrate therapy caused a stability of bone density in the distal third of the radius. The fractional change in bone density was −0.007 at 1 year, −0.005 at 2 years, −0.002 at 3 years and +0.008 at 4 years to avoid impeding calcium absorption. Fifth, the ratio of citrate to phosphorous (primary as phosphate) is preferably above about 0.5, most preferably above about 5.6.

The following examples are presented to describe preferred embodiments and utilities of the present invention and are not meant to limit the present invention unless otherwise stated in the claims appended hereto.

EXAMPLE 1

Formulation of Pre-Mixes of Calcium Hydroxide and Citric Acid

Two formulations of the pre-mix with a calcium/citrate molar ratio of 1.25 were made in order to provide orange and lemon-lime flavor preparations.

The orange flavored preparation (each 234.2 g) contained 153.6 g citric acid, 74.0 g $Ca(OH)_2$, 2.4 g orange flavoring, 4.0 g aspartame, 150 mg vitamin $B_2$, and 22 mg of Red No. 40-89%. Each 2.927 g of this material, which could be placed in an individual sachet or scoop, contained 500 mg of elemental calcium.

The lemon-lime flavored preparation (each 232.3 g) contained 153.6 g citric acid, 74.0 g $Ca(OH)_2$, 1.7 g lemon-lime flavoring, 2.85 g aspartame, and 115 mg of vitamine $B_2$. Each 2.903 g of this material provided 500 mg of elemental calcium.

When 500 mg calcium amounts of above materials were suspended in 300 ml of water, they dissolved very rapidly and produced a well-tolerated drink of satisfactory flavor.

In order to prevent clumping of powdered mixtures, Cabosil (fumed silica NF) may be added.

EXAMPLE 2

Solubility of Mixtures of Calcium Hydroxide and Citric Acid with a Calcium Citrate Molar Ratio of 1.25

The aqueous solubility of a mixture of calcium hydroxide and citric acid with a calcium/citrate molar ratio of 1.25 was determined as follows. A sufficient amount of the mixture containing 500 mg of elemental calcium was suspended in 300 ml of water kept at 37° C. and at various pHs (2-7) while the pH was maintained at the predetermined level. After 1, 2 and 24 hours of incubation, the filtrate was analyzed for calcium. The amount of calcium recovered in the filtrate represented solubility, where 100% recovery indicated complete solubility.

The pre-mix dissolved in water very rapidly (within 2 minutes). It remained in solution after 1 hour of incubation (Table 1). After 2 hours of incubation, crystallization of calcium citrate occurred at pH greater than 4.5, indicated by an appearance of visible precipitate and a decline in calcium recovery. Below pH 4.5, the pre-mix was completely soluble. After 24 hours of incubation, precipitation was noticeable at pH greater than 3.5. The filtrate concentration of calcium was much lower than at an earlier period of incubation (2 hours). The curve representing the solubility of precipitated calcium citrate from the dissolved pre-mix was indistiguishable from that of pre-formed calcium citrate (solid) of identical calcium/citrate ratio. The results suggested that at steady state conditions (24 hours of incubation), the final crystalline material (and its solubility) was the same whether it was obtained from dissolution of the preformed calcium citrate or from precipitation from dissolved pre-mix of calcium hydroxide and citric acid. The advantage of the pre-mix is that this device allows for a preparation of a liquid formulation of calcium citrate much more rapidly and at a higher calcium concentration than might be possible from preformed solid calcium citrate.

TABLE 1

| Solubility of Pre-mix of Calcium Hydroxide and Citric Acid with Calcium/Citrate Molar Ratio of 1.25 Percent of Calcium Recovered in the Filtrate | | | |
|---|---|---|---|
| pH | 1 hr | 2 hr | 24 hr |
| 2.0 | 99.3 | 99.6 | 99.0 |
| 2.5 | 99.3 | 99.0 | 97.8 |
| 3.0 | 98.1 | 98.6 | 94.6 |
| 3.5 | 97.8 | 98.4 | 95.9 |
| 4.0 | 97.8 | 97.4 | 35.6 |
| 4.5 | 97.5 | 95.4 | 17.2 |
| 5.0 | 91.2 | 73.9 | 15.0 |
| 6.0 | 95.7 | 63.8 | 19.1 |
| 7.0 | 95.4 | 58.9 | 22.0 |

EXAMPLE 3

Relative solubility of Different Pre-Mixes of Calcium Hydroxide and Citric Acid The solubility of various pre-mixes (calcium/citrate molar ratio of 1.5, 1.25 and 0.67) was determined as described in Example 2, and compared with that of tricalcium dicitrate (also 500 mg calcium per 300 ml). After 2 hours of incubation, tricalcium dicitrate displayed expected solubility, with high dissolution at low pHs and reduced/limited dissolution at high pHs (Table 2). The pre-mix of calcium hydroxide and citric acid with an identical calcium/citrate molar ratio of 1.5 had a much higher solubility. Both preparations were completely soluble or nearly so at a pH of 2.0 and 2.5. At higher pHs, the pre-mix gave a much greater calcium recovery at this early period of incubation.

The pre-mixes with an excess of citric acid (calcium/citrate molar ratios of 1.25 and 0.67) had an even greater solubility. The preparation with the highest solubility was the pre-mix with calcium/citrate molar ratio of 0.67. It was completely soluble even at high pHs.

Thus, pre-mixes with an excess of citric acid (for example, calcium/citrate molar ratio of 1.25 and 0.67) allowed more calcium to remain in solution even in the neutral pH of the intestinal juice (where calcium absorption takes place), than the pre-mix with the calcium/citrate ratio of tricalcium dicitrate, i.e. — 1.5.

TABLE 2

Solubility of Different Pre-Mixes
After 2 Hours of Incubation
Percent of Calcium Recovered in the Filtrate

| pH | Pre-Mix (1.5) | Pre-Mix (1.25) | Pre-Mix (0.67) | Tricalcium Dicitrate |
|---|---|---|---|---|
| 2.0 | 99.6 | 99.6 | 98.6 | 95.1 |
| 2.5 | 99.5 | 99.0 | 99.7 | 95.0 |
| 3.0 | 100.0 | 98.6 | 99.2 | 83.6 |
| 3.5 | 99.5 | 98.4 | 99.4 | 61.3 |
| 4.0 | 99.1 | 97.4 | 99.2 | 39.9 |
| 4.5 | — | 95.4 | 91.7 | 25.3 |
| 5.0 | 98.7 | 73.9 | 52.1 | 16.9 |
| 6.0 | 99.2 | 63.8 | 37.6 | 14.9 |
| 7.0 | 96.3 | 58.7 | 38.8 | 14.3 |

Numbers below Pre-mix in parentheses indicate the calcium/citrate molar ratio in this and subsequent tables.

EXAMPLE 4

Absorption of Calcium from Different Pre-Mixes Assessed by an Indirect Method of Oral Calcium Loading Calcium adsorption was measured indirectly in 10 normal subjects from the rise in their urinary calcium after ingestion of 500 mg calcium as a liquid formulation of various pre-mixes or as a solid preparation of tricalcium dicitrate. The increment in urinary calcium during the second two hours following oral calcium load was substantially higher after taking dissolved pre-mixes than after ingestion of solid tricalcium dicitrate (Table 3). This indirect measure of calcium absorption was greatest for the pre-mix with a calcium/citrate molar ratio of 1.25 than for other pre-mixes.

Thus, calcium was more bioavailable from liquid preparations of the pre-mixes than from solid tricalcium dicitrate.

TABLE 3

Indirect Measure of Calcium Absorption from Pre-Mixes
Increment in Urinary Calcium

TABLE 3-continued

Indirect Measure of Calcium Absorption from Pre-Mixes

| Calcium Preparation | (mg calcium/100 ml glomerular filtrate) |
|---|---|
| Tricalcium dicitrate (1.5) | 0.087 ± 0.087 |
| Pre-mixes | |
| (1.5) | 0.142 ± 0.061** |
| (1.25) | 0.151 ± 0.061** |
| (0.67) | 0.103 ± 0.059 |

Values are presented as mean ± SD. Significant difference from triclcium dicitrate is shown by ** for $p < 0.01$.

EXAMPLE 5

Calcium Absorption from Pre-Mixes Using a More Direct Method

In 6 normal subjects, intestinal calcium absorption was indirectly measured from the fecal recovery of radioactive calcium after giving by mouth liquid preparations of various pre-mixes or tricalcium dicitrate (solid preparation) pre-labeled with radiocalcium. The calcium absorption from pre-mixes was higher than from tricalcium dicitrate (Table 4). The highest absorption was obtained with the mixture of calcium hydroxide and citric acid with a calcium/citrate molar ratio of 1.25.

TABLE 4

Radiocalcium Absorption from Pre-Mixes

| Calcium Preparation | Calcium Absorption (%) |
|---|---|
| Tricalcium dicitrate (1.5) | 19.1 ± 6.9 |
| Pre-mix | |
| (1.5) | 24.3 ± 10.2 |
| (1.25) | 32.5 ± 5.3* |
| (0.67) | 23.9 ± 13.5 |

Values are presented as mean ± SD. Significant difference from tricalcium dicitrate is shown by * for $p < 0.05$.

EXAMPLE 6

Effect of Pre-Mix Administration on Urinary Citrate

Following oral administration of 500 mg calcium as various pre-mixes (in a liquid form) or as tricalcium dicitrate (solid), urinary citrate was measured over 4 hours in 10 normal subjects (Table 5). As compared to the control value obtained without taking any calcium, urinary citrate was greater after receiving liquid calcium supplements from pre-mix with calcium/citrate molar ratio of 1.25 and 0.67 (citrate-rich preparations).

TABLE 5

Urinary Citrate Following Oral Administration of Pre-Mixes

| Calcium Preparation | Urinary Citrate (mg/4 hour) |
|---|---|
| Tricalcium dicitrate (1.5) | 120 ± 33 |
| Pre-mix | |
| (1.5) | 118 ± 33 |
| (1.25) | 137 ± 50 |
| (0.67) | 174 ± 35+ |
| Control | 120 ± 30 |

Values are presented as mean ± SD. Significant difference from the control (without calcium supplementation) is shown by ± for $p < 0.001$.

EXAMPLE 7

Summary of Properties of Various Calcium Preparations

The mixture of calcium hydroxide and citric acid with a calcium/citrate molar ratio of 0.67 (citrate-rich) was most soluble, and had the greatest citrate content and citraturic action (Table 6). However, it had the lowest calcium bioavailability among the pre-mixes. The pre-mix with a calcium/citrate molar ratio for 1.25 had the highest calcium bioavailability, and had adequate solubility, citrate content and citraturic action. Assuming a recommended calcium intake of 1 g/day, the amount of citrate contained in this pre-mix was 60 meq/day, a safe level.

These varying properties might be utilized to special advantage under different clinical conditions, to suit particular needs of those conditions.

TABLE 6
Order of Efficiency of Different Calcium Preparations

|  | Pre-Mixes | | | Tricalcium |
|---|---|---|---|---|
|  | (1.5) | (1.25) | (0.67) | Dicitrate |
| Solubility | 3 | 2 | 1 | 4 |
| Ca bioavailability | 2 | 1 | 3 | 4 |
| Citraturic action | 3 | 2 | 1 | 3 |
| Citrate content | 3 | 2 | 1 | 3 |

EXAMPLE 8

Solubility of Ca(OH)$_2$ and CaCO$_3$ in Orange Juice

Since orange juice is rich in citric acid, addition of calcium hydroxide or calcium carbonate results in the formation of calcium citrate. The following general stoichiometric reaction formulas indicate appropriate reactions.

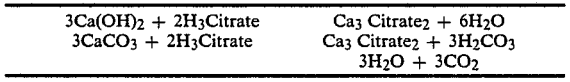

$$3Ca(OH)_2 + 2H_3Citrate \rightarrow Ca_3Citrate_2 + 6H_2O$$
$$3CaCO_3 + 2H_3Citrate \rightarrow Ca_3Citrate_2 + 3H_2CO_3$$
$$\rightarrow 3H_2O + 3CO_2$$

Solubility of calcium hydroxide was determined in Minute Maid orange juice (concentrate diluted 1:3 with distilled water) at 6° C. (refrigerated). This "diluted" juice (hereafter called simply orange juice) contained 45 mmoles of total citrate/liter; pH was 3.91. Increasing amounts of calcium hydroxide were added to 180 ml (6 oz) of orange juice, and stirred for 30 minutes. The filtrate of the stirred mixture was assayed for pH and calcium content (Table 7).

TABLE 7
Solubility of Calcium Hydroxide in Orange Juice

| Sample | Amount of Ca added as Ca(OH)$_2$ (mg Ca) | Final pH | Filtrate Ca mg/180 ml |
|---|---|---|---|
| 1 | 100 | 4.15 | 106 |
| 2 | 200 | 4.44 | 204 |
| 3 | 300 | 4.83 | 305 |
| 4 | 400 | 7.44 | 401 |
| 5 | 500 | 9.16 | 418 |

Calcium hydroxide readily dissolved (within 5 minutes) in samples 1 and 2. It dissolved more slowly (20 minutes) in sample 3. Samples 1–3 retained the original orange juice color. The final pH was less than 4.9 and final filtrate calcium closely approximated the amount added. However, in samples 4 and 5, final pH was much higher and there was grayish discoloration. Incomplete dissolution of calcium hydroxide was confirmed by the lower final filtrate concentration of calcium (compared to amount added) in Sample 5.

The results suggested that there is sufficient amount of free citric acid in orange juice to convert up to 300 mg calcium as calcium hydroxide/180 ml into soluble calcium citrate.

Similar results were obtained when calcium carbonate was added to orange juice. For example, when 300 mg calcium as calcium carbonate was added to 180 ml of Minute Maid orange juice (refrigerated), it dissolved rapidly (within 5 minutes). However, foam developed due to the elaboration of carbon dioxide. A mixture of calcium carbonate and calcium hydroxide (100 mg Ca as calcium carbonate and 200 mg calcium as calcium hydroxide) was added to 180 ml of orange juice. Rapid dissolution (within 5 minutes) again took place. There was less foam.

Thus, addition of calcium carbonate either alone or with calcium hydroxide provides rapid dissolution in orange juice. Unfortunately, the development of foam may limit the usefulness of calcium carbonate. Dissolution of calcium carbonate and citric acid in aqueous solutions or juices other than those as prone to foaming as orange juice is likely to be feasible to form a desired calcium compound/citric acid mixture analogously useful to the calcium hydroxide/citric acid combinations described earlier herein.

Changes may be made in the compounds and procedures described herein without departing from the concept and scope of the invention as defined in the following claims.

What is claimed is:

1. A composition of matter consisting essentially of calcium hydroxide and citric acid in a calcium hydroxide/citric acid molar ratio between about 0.6 and about 3.0.

2. A composition of matter for dissolution in water to form a liquid dietary calcium supplement comprising soluble calcium citrate, the composition of matter being substantially dry and consisting essentially of citric acid and a calcium compound selected from the group consisting of calcium hydroxide, calcium carbonate and calcium oxide, the composition of matter being further characterized in that the calcium compound and citric acid are in a calcium compound/citric acid molar ratio between about 0.6 and about 3.0.

3. The composition of matter of claim 1 or 2 defined further as comprising one or more of a flavorant, lubricant, sweetener or colorant.

4. The composition of matter of claim 1 or 2 defined further as having a calcium compound/citric acid or calcium hydroxide/citric acid molar ratio of about 1.25.

5. A soluble calcium dietary supplement consisting of a dry premix of calcium carbonate and citric acid in a molar ratio in the range of about 0.67 to about 1.25.

6. A pharmaceutical composition for the dietary calcium supplementation of a subject, the composition comprising a mixture of calcium hydroxide and citric acid in a calcium hydroxide/citric acid molar ratio of between about 0.67 and 1.25

7. The pharmaceutical composition of claim 6 wherein the calcium hydroxide/citric acid molar ratio is about 1.25.

8. A potable liquid suitable for dietary supplementation of calcium without substantial risk of calcium renal stone facilitation or enhancement the preparation consisting essentially of:

a calcium compound selected from the group consisting of calcium hydroxide, calcium oxide and calcium carbonate;

citric acid; and water.

9. The potable liquid of claim 8 defined further as having a pH between about 2 and about 7.

10. The potable liquid of claim 8 defined further as having a pH between about 3 and about 5.

11. The potable liquid of claim 8 defined further wherein the calcium compound and citric acid are in a calcium compound/citric acid molar ratio between about 0.6 and about 3.0.

12. The potable liquid of claim 8 defined further as comprising calcium in a concentration between about 500 mg/L and about 2000 mg/L.

13. The potable liquid of claim 8 wherein the calcium compound is defined further as being calcium hydroxide.

14. The potable liquid of claim 8 defined further wherein the calcium compound and citric acid are in a calcium compound/citric acid molar ratio between about 0.6 and about 1.5.

15. A method for preparing a mixture, said mixture being soluble in an aqueous solvent to form a potable liquid consisting essentially of calcium citrate, the method comprising mixing calcium hydroxide and citric acid a calcium hydroxide/citric acid molar ratio of between about 0.6 and about 3.0.

16. A method for preparing a potable liquid consisitng essentially of calcium citrate and citric acid, the method comprising:

(a) preparing a mixture comprising calcium hydroxide and citric acid in a calcium hydroxide/citric acid molar ratio of between about 0.60 and about 3.0; and (b) dissolving a quantity of said mixture in an amount of aqueous solvent to produce a solution comprising calcium in a concentration between about 500/mg L and 2000 mg/L.

17. A method of preparing a pharmaceutical composition for dietary calcium supplementation of a subject comprising the steps of:

(a) combining weighed quantities of calcium compound and citric acid at a calcium/citrate molar ratio of about 1.25 so as to form a dry premix; and (b) adding a volume of an aqueous solvent to the premix of step (a) to dissolve said premix.

18. A method for supplementing dietary calcium comprising administration of a mixture of calcium hydroxide and citric acid in a calcium hydroxide/citric acid molar ratio of between about 0.67 and about 1.5.

19. The method of claim 18 wherein the mixture is further defined as having a calcium concentration of between about 500 mg/L and 2,000 mg/L.

20. A method for supplementing dietary calcium comprising:

(a) preparing a premix of calcium hydroxide and citric acid with a calcium hydroxide/citric acid molar ratio of between about 0.67 and about 1.25;

(b) dissolving said premix to form a potable liquid in a volume of aqueous solvent sufficient to achieve a calcium concentration of between 500 mg/L to about 2,000 mg/L; and (c) ingesting said potable liquid daily at a dose of about 60 meq. calcium/day.

* * * * *